(12) United States Patent
Elsheikh et al.

(10) Patent No.: US 8,987,535 B2
(45) Date of Patent: *Mar. 24, 2015

(54) PROCESS FOR THE MANUFACTURE OF HYDROCHLOROFLUOROOLEFINS

(71) Applicant: Arkema Inc., King of Prussia, PA (US)

(72) Inventors: Maher Y. Elsheikh, Wayne, PA (US); Anne Pigamo, Francheville (FR); Sri R. Seshadri, Holland, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/183,828

(22) Filed: Feb. 19, 2014

(65) Prior Publication Data

US 2014/0171698 A1  Jun. 19, 2014

Related U.S. Application Data

(63) Continuation-in-part of application No. 14/167,150, filed on Jan. 29, 2014, which is a continuation-in-part of application No. 13/127,817, filed as application No. PCT/US2009/064145 on Nov. 12, 2009, now Pat. No. 8,642,819.

(60) Provisional application No. 61/116,056, filed on Nov. 19, 2008.

(51) Int. Cl.
| | |
|---|---|
| C07C 19/08 | (2006.01) |
| C07C 17/358 | (2006.01) |
| C07C 17/20 | (2006.01) |
| C07C 17/25 | (2006.01) |
| C07C 17/275 | (2006.01) |
| C07C 17/278 | (2006.01) |
| C07C 17/38 | (2006.01) |
| C07C 17/383 | (2006.01) |

(52) U.S. Cl.
CPC ............ *C07C 17/358* (2013.01); *C07C 17/206* (2013.01); *C07C 17/25* (2013.01); *C07C 17/275* (2013.01); *C07C 17/278* (2013.01); *C07C 17/38* (2013.01); *C07C 17/383* (2013.01); *C07B 2200/09* (2013.01)
USPC .......................................... 570/170; 570/151

(58) Field of Classification Search
None
See application file for complete search history.

(56) References Cited

U.S. PATENT DOCUMENTS

| | | |
|---|---|---|
| 5,616,189 A | 4/1997 | Jin et al. |
| 5,616,819 A | 4/1997 | Boyce et al. |
| 5,710,352 A | 1/1998 | Tung et al. |
| 5,811,603 A | 9/1998 | Elsheikh |
| 5,877,359 A | 3/1999 | Elsheikh |
| 6,166,274 A | 12/2000 | Chen et al. |
| 6,881,698 B2 | 4/2005 | Bonnet et al. |
| 7,420,094 B2 | 9/2008 | Petrov et al. |
| 8,642,819 B2 * | 2/2014 | Elsheikh et al. .............. 570/170 |
| 2005/0177012 A1 | 8/2005 | Cohn et al. |
| 2008/0051610 A1 | 2/2008 | Wang et al. |
| 2008/0051611 A1 | 2/2008 | Wang et al. |
| 2008/0103342 A1 | 5/2008 | Wang et al. |

* cited by examiner

*Primary Examiner* — Sudhakar Katakam
(74) *Attorney, Agent, or Firm* — Steven D. Boyd

(57) ABSTRACT

The invention also relates a process for the manufacture of trans 1-chloro3,3,3-trifluoropropene. The process comprises an isomerization step from cis 1233zd to trans 1233zd.

15 Claims, 1 Drawing Sheet

PROCESS FOR THE MANUFACTURE OF HYDROCHLOROFLUOROOLEFINS

This application is a Continuation-In-Part of U.S. application Ser. No. 14/167,150 filed Jan. 29, 2014, which is a Continuation-In-Part of U.S. application Ser. No. 13/127817 filed May 5, 2011 (U.S. Pat. No. 8,642,819), which claims priority to International application serial number PCT/US09/64145 filed Nov. 11, 2013 and U.S. Provisional application Ser. No. 61/116,056 filed Nov. 19, 2008, all incorporated herein by reference.

FIELD OF THE INVENTION

The present invention relates to a process for the manufacture of hydrochlorofluoroolefins.

BACKGROUND OF THE INVENTION

The Montreal Protocol for the protection of the ozone layer mandates the phase out of the use of chlorofluorocarbons (CFCs). Materials more "friendly" to the ozone layer such as hydrofluorocarbons (HFCs) e.g. 134a replaced chlorofluorocarbons. The latter compounds have proven to be greenhouse gases, causing global warming and could be regulated by the Kyoto Protocol on Climate Change. Replacement materials are needed which are environmentally acceptable i.e. have negligible ozone depletion potential (ODP) and acceptable low global warming potential (GWP). The present invention describes a process for manufacturing of the hydrochlorofluoroolefin, trans 1233zd (E-1233zd, 1-chloro-3,3,3-trifluoropropene) which is useful as a low ODP and low GWP blowing agent for thermoset and thermoplastic foams, solvent, heat transfer fluid such as in heat pumps, and refrigerant such as a low pressure refrigerant for chillers.

US patent publications US2008/0051610 and US2008/0103342 disclose a process that includes a step of the catalytic isomerization of cis 1234ze to trans 1234ze. U.S. Pat. No. 7,420,094 discloses the isomerization of 1234ze to 1234yf with a Cr based catalyst. U.S. Pat. No. 8,217,208 discloses a process of isomerization of one isomer of 1-chloro-3,3,3-trifluoropropene to the other isomer including the step of contacting a feed stream with a heated surface. US2008/0051611 discloses the recovery of trans 1234ze from a mixture that includes cis 1234ze and trans1234ze via distillation.

SUMMARY OF THE INVENTION

The present invention relates a process for the manufacture of the hydrochlorofluoroolefin, trans 1-chloro-3,3,3-trifluoropropene (E-1233zd). The process comprises an isomerization step from cis 1233zd (Z-1233zd) to trans 1233zd (E-1233zd).

DETAILED DESCRIPTION OF THE INVENTION

Figure 1:
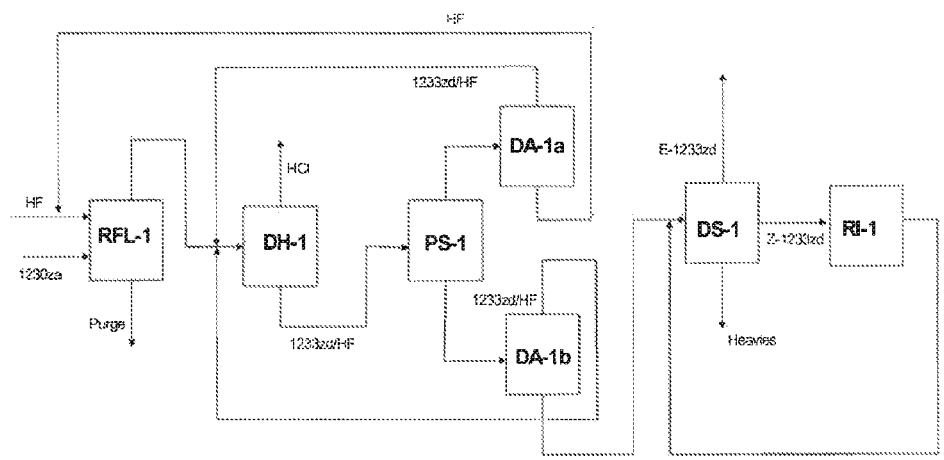
FIG. 1 is a schematic of a liquid phase process in accordance with the present invention.

The present invention provides a process for the manufacture of trans 1-chloro-3,3,3-trifluoropropene (E-1233zd). The first step of the process comprises forming a chloroalkane via addition of an olefin to a starting chloroalkane and reacting the chloroalkane to form 1,1,3,3-tetrachlororopropene (1230za, $CCl_2$=CH—$CHCl_2$) and/or 1,1,1,3,3-pentachloropropane (240fa). That step is followed by a fluorination step comprising the fluorination of 1,1,3,3-tetrachlororopropene (1230za, $CCl_2$=CH—$CHCl_2$) and/or 1,1,1,3,3-pentachloropropane (240fa) to a mixture of cis 1233zd (Z-1233zd) and trans 1233zd (E-1233zd). That step is followed by a separation step that comprises a separation of the mixture formed in the first step to isolate cis 1233zd (Z-1233zd) from the mixture. That step is followed by an isomerization step that comprises isomerization of cis 1233zd (Z-1233zd) to trans 1233zd (E-1233zd).

The 1,1,1,3,3-pentachloropropane (240fa) or 1,1,3,3-tetrachloropropene (1230za) feedstocks are chlorinated compounds generally manufactured using addition reactions followed by a step such as chloroination or dehydrohalogenation.

The production of chloroalkanes such as 240fa, 250fb, 240db, and 230da by the addition of olefin to a starting chloroalkane is well-known in the art. For example, 240fa is generally manufactured by the addition of carbon tetrachloride to vinyl chloride using a catalyst and a co-catalyst. The co-catalyst is typically an organic ligand capable of forming a complex with the catalyst to bringing the catalyst into solution. The process may be carried out batch wise or preferably in a continuous mode. The production system may be closed to provide complete recycle of the unreacted feed material haloalkane and haloalkene.

Useful starting chlorooalkane raw materials for the preparation of the 1,1,1,3,3-pentachloropropane (240fa) or 1,1,3,3-tetrachloropropene (1230za) feedstocks of the present invention include carbon tetrachloride, chloroform and methyl chloride while useful olefins include ethylene, vinyl chloride, 1,1-dichloroethene, 1,2-dichloroethene, trichloroethylene, tetrachlorethylene and chlorofluoroethylene.

Exemplary reactions of a starting chloroalkane and olefin include:
  addition of carbon tetrachloride to ethylene to provide 1,1,1,3-tetrachloropropane (250fb)
  addition of carbon tetrachloride to vinyl chloride to provide 1,1,1,3,3-pentachloropropane (240fa)
  addition of methylene chloride to trichloroethylene to provide 1,1,1,2,3-pentachloropropane (240db)
  addition of carbon tetrachloride to 1,2-dichloroethylene to provide 1,1,1,2,3,3-hexachloropropane (230da)

The catalysts useful in reactions of a starting chloroalkane and olefin include cuprous compounds, iron powder, iron chloride, organonickel compound catalyst or organocopper catalyst. Co-catalysts can be selected from chelating agents and may serve as solvents. Suitable ligands are selected from amines, amides, nitriles and organophosphate solvents.

The chloroalkanes produced, such as 240fa, 250fb, 240db, and 230da are further reacted such as via chlorination or dehydrochlorination to produce the desired 1,1,1,3,3-pentachloropropane (240fa) or 1,1,3,3-tetrachloropropene (1230za) feedstocks.

In one embodiment, the further reaction is a chlorination step. More specifically, 250fb can be chlorinated to produce a mixture of 1,1,1,3,3-pentachloropropane (240fa) and 1,1,1,2,3-pentachloropropane (240db). This chlorination may be accomplished via photochlorination.

In a second embodiment, the further reaction is a dehydrochlorination step. More specifically, 240fa can be dehydrochlorinated to obtain 1230za. The dehydrochlorination step can be carried out with gas or liquid phase process in the presence or absence of a catalyst.

In a third embodiment, the further reaction is a dechlorination step. More specifically, 230da can be dechlorinated to provide 1230za. Methods known in the art can be used to complete this dechlorination, such as the use of zinc dust to complete this dechlorination reaction.

The present invention is directed toward a process for producing trans 1-chloro-3,3,3-trifluoro propene (E-1233zd) from 1,1,3,3-tetrachlororopropene (1230za, $CCl_2$=CH—$CHCl_2$) and/or 1,1,1,3,3-tetrachloropropane (240fa) that comprises the steps of:

a) forming a chloroalkane via addition of an olefin to a starting chloroalkane and reacting the chloroalkane to form 1,1,3,3-tetrachlororopropene (1230za, $CCl_2$=CH—$CHCl_2$) and/or 1,1,1,3,3-pentachoropropane (240fa); followed by b) fluorination of 1,1,3,3-tetrachlororopropene (1230za, $CCl_2$=CH—$CHCl_2$) and/or 1,1,1,3,3-pentachoropropane (240fa) in gas phase, or liquid phase fluorination of 1230za to obtain a mixture of cis (Z) and trans (E) 1-chloro-3,3,3 trifluoro propene (1233zd, $CF_3$—CH=CHCl); followed by c) separation of cis (Z) 1-chloro 3,3,3-trifluoropropene (1233zd, $CF_3$—CH=CHCl) and trans (E) 1-chloro 3,3,3-trifluoropropene (1233zd, $CF_3$—CH=CHCl); followed by d) isomerization of the cis 1233zd (Z-1233zd) from the second step to form trans 1233zd (E-1233zd).

The fluorination step of the process, gas phase fluorination of 1230za and/or 240fa to 1233zd or liquid phase fluorination of 1230za to 12333zd; can be via any process known in the art. For example: the uncatalyzed liquid phase fluorination of 1230za is disclosed in U.S. Pat. No. 5,877,359; the catalyzed gas phase fluorination of 1230za is disclosed in U.S. Pat. No. 5,811,603; U.S. Pat. No. 6,166,274 discloses the fluorination of 1230za to 1233zd in the presence of catalyst such as trifluoroacetic acid or triflic acid. Fluorination catalysts such as $TiCl_4$, $TiF_4$, $SnCl_4$, $SnF_4$, $SbF_5$, $SbCl_5$, $SbF_xCl_y$ (x+y=5), or an ionic liquid are described in U.S. Pat. No. 6,881,698. When an Sb type catalyst is used, it is preferred to feed low level of $Cl_2$ to maintain the Sb species in an active form.

The separation step of the process comprises the separation of the cis 1233zd and trans 1233zd formed in the first step via an appropriate separation means such as distillation, liquid phase separation, or extractive separation. The cis 1233zd and trans 1233zd formed in the first step may contain HF and HCl. Preferably, the HCl is first removed in a first distillation column. Thereafter, liquid phase separation coupled with azeotropic distillation can be used to remove HF. The boiling point difference of cis 1233zd and trans 1233zd enable them to be separated by conventional distillation, typically at atmospheric pressures.

The isomerization step of the process involves the isomerization of the cis 1233zd from the separation step into trans 1233zd. The isomerization step can be carried out in the gas phase using a heterogeneous or in the liquid phase uncatalyzed reaction or a liquid phase catalyzed reaction using a homogeneous catalyst.

The isomerization step is achievable with a gas phase process in the presence of a heterogeneous catalyst. A suitable heterogeneous catalyst is high surface area $Cr^{(III)}$ catalyst, supported or unsupported, that can optionally contains low levels of one or more co-catalysts selected from cobalt, nickel, zinc or manganese. For supported catalyst, the catalyst support can be selected from materials known in the art to be compatible with high temperature and pressure processes. For example, fluorinated alumina, HF treated activated carbon or carbon graphite are suitable catalyst supports. A preferred catalyst is a high surface area unsupported chromium oxide catalyst that is activated with HF before use, optionally at pressure above 50 psi. The level of the co-catalyst, when present, can be varied from 1 to 10 weight %, preferably from 1 to 5 weight % of the catalyst. Co-catalyst can be added to the catalyst by processes known in the art such as adsorption from an aqueous or organic solvent, followed by solvent evaporation.

Suitable heterogeneous catalyst can also be selected from: Lewis acids supported catalysts selected from $Sb^V$, $Ti^{IV}$, $Sn^{IV}$, $Mo^{VI}$, $Nb^V$ and $Ta^V$. The support itself is selected from the group such as fluorinated alumina; fluorinated chromia; HF activated carbon or graphite carbon. Supported antimony halides such as $SbF_5$ are described in U.S. Pat. No. 6,528,691 and are preferred catalysts. Other solid catalysts such as NAFION® type polymer, acidic molecular sieves and, zeolites can be also used.

For the gas phase process, the temperature can be varied between 20-500° C., preferably between 100-400° C. Contact times can vary from 0.5 to 100 seconds. A low level of oxidizing agent such as oxygen or oxygen containing gas such as air or chlorine gas can be used at between 0.01-0.1 volume percent to prolong the life of the catalyst.

The isomerization step is also achievable in a liquid phase process in an uncatalyzed reaction or a catalyzed reaction in the presence of a homogenous catalyst preferably selected from compounds of group 3, 4, 5, 13, 14 and 15 metal compounds of the Periodic Table of the elements (IUPAC 1988) and their mixtures (groups of the Periodic Table of the elements which were previously called IIIA, IVa, IVb, Va, Vb and VIb). The compounds of the metals are intended to include hydroxides, oxides and the organic or inorganic salts of these metals, as well as mixtures thereof. Preferred are the aluminum, titanium, tantalum, molybdenum, boron, tin and antimony derivatives such as $AlCl_3$, $TiCl_4$, $TaCl_5$, $MoCl_6$, $BF_3$, $SnCl_4$, and $SbCl_5$. In the process according to the invention the preferred derivatives of the metals are the salts and these are preferably chosen from the halides and more particularly from chlorides, fluorides and chlorofluorides such as $AlF_3$, $TiF_4$, $TaF_5$, $MoF_6$, $SnF_4$, $SbF_5$, $SbF_xCl_y$ (x+y)=5. The catalyst must be subjected to activation (by HF or any molecule able to exchange fluorine) prior to the isomerization step. In the case of antimony type catalyst, a low level of chlorine gas as oxidizing agent can be used to maintain the antimony catalyst in the pentavalent oxidation state. In addition to the above mentioned Lewis acids catalyst, an ionic liquid derived from antimony, titanium, niobium and tantalum is suitable for liquid phase fluorination processes. A description of the preparation of such catalysts is disclosed in the U.S. Pat. No. 6,881,698.

The homogenous catalyst for a liquid phase catalyzed process can also be selected from the Bronsted type family of acids such as (but not limited to) sulfuric acid $H_2SO_4$, sulfonic type acids such as $ClSO_3H$ or $FSO_3H$ or triflic acid $CF_3SO_3H$ or methane sulfonic acid $CH_3SO_3H$. For the liquid phase process, the operating temperature can be varied between about 20-200° C., with a contact time between about 0.5-50 hours.

The process of the present invention may comprise additional separation steps between each step. The purpose of theses separations could be:

1. to remove, totally or partially, any hydracid (HF, HCl) from the flow if required, or
2. to isolate a desired product in order to feed it in a subsequent step, or
3. to purify a product and removes organic impurities or by products, or 4. to dry a product (H$_2$O removal).

The means used to achieve these additional steps are known in the art and include but are not limited to: distillation, extractive distillation or adsorption.

The process of the present invention is exemplified in the figures, which set forth block flow diagrams of gas phase and liquid phase processes in accordance with the present invention. The processes in the figures are set out in the form of process modules designed to achieve a specific purpose and arranged in accordance with the process of the present invention. Theses modules comprise:

RFL—comprises a liquid phase fluorination reactor and rectification system comprising an unagitated, jacketed pressure vessel connected to a rectification column. The reactor also acts as the reboiler of the rectification column. The HF and organic (1230za) are fed directly to the reactor. The molar feed ratio of HF to organic is dictated by the reaction stoichiometry and the amount of HF leaving the reactor with the rectification column overhead and liquid phase purges. Mixing is provided by the boiling action of the reactor contents. For the most part, the reactor effluent leaves the reactor vessel as a gas and enters the bottom of the rectification column. A small purge from the liquid phase can remove any non-volatiles that may form during the reaction. The rectification column contains either packing or trays designed to provide good mass transfer between up flowing gas and down flowing liquid. The condenser at the top of the column is cooled by either cooling water, chilled water, or some type of refrigeration. The condenser is a partial condenser where the liquid effluent is refluxed directly back to the column. The vapor effluent consists of HCl, HF and organic components.

DH—comprises an HCl distillation system whereby pure HCl is removed from the top of a distillation column. This column can operate between 100 psig and 300 psig. More typically, the HCl is distilled above 120 psig to allow the use of conventional (−40 C) refrigeration at the top of the HCl column. The bottoms of this column contains HF and organic with a small residual amount of HCl. The ratio of HF to the organic component typically is close to the azeotropic composition.

PS—comprises a liquid phase separator to separate two liquid phases, one consisting primarily of a hydrochlorofluorocarbon (HCFC) and the other consisting primarily of HF. The HF phase is usually the less dense so that it exits from the top of the phase separator and the HCFC exits as the bottom phase. There is some HF in the HCFC phase and some HCFC in the HF phase. However, the compositions of both phases are far removed from any azeotropic composition. The operating temperature of the phase separator can be between −40° C. and +20° C. However, the lower the temperature, the better the phase separation.

DA—comprises an azeotropic distillation column which distills overhead an azeotropic composition of HF and an organic consisting of one or more HCFC's (hydrochlorofluorocarbons) and HFC's (hydrofluorocarbons). These organic compounds can be either saturated or olefinic. The bottoms composition is either entirely HF or entirely organic, depending on whether the column feed composition is on the HF rich side or the organic rich side of the azeotrope. If the bottoms are HF, this stream is normally recycled back to the reactor. If the bottoms steam is organic, it is sent to a conventional distillation train.

DS—comprises a straight distillation normally done under pressure.

RI—comprises a gas phase isomerization reaction typically done at temperatures above 400° C. in an adiabatic, packed bed reactor. The module consists of a feed vaporizer and superheater. It can include an "economizer", whereby hot effluent is fed to one side and relatively cold reactor feed gases are fed to another side of a heat exchanger. The effluent gases are further cooled before entering a distillation column. Isomerization reactions can be run at varying conversions depending on the equilibrium distribution of isomers. The effluent isomers can have boiling points very close together. However, they typically exhibit close to ideal behavior so can be separated by conventional distillation. As an alternative to the gas phase, this reaction can be done as a homogeneously catalyzed liquid phase reaction. In this configuration, the reactor would be a continuous stirred tank with the effluent being removed as a vapor to effect separation from the catalyst.

RFG—comprises a gas phase fluorination reactor that is an adiabatic packed bed reactor that feeds a gas phase over a solid catalyst. No cooling is needed because of the reactor has a low conversion per pass and a high HF molar feed ratio. The adiabatic exotherm is typically less than 100° C. The feed HF and organic are vaporized in a common vaporizer and superheated to the reactor temperature. The common vaporizer allows the 1230za and/or 240fa to be vaporized at a lower temperature than would be possible if it were vaporized as a pure component, thereby minimizing thermal degradation. This module can also include an "economizer", whereby hot effluent is fed to one side and relatively cold reactor feed gases are fed to another side of a heat exchanger. The effluent gases are further cooled before entering a distillation column. Reaction temperatures are between 200° C. and 400° C. The pressure is high enough to allow the HCl by-product to be distilled with conventional refrigeration—preferably between 100 psig and 200 psig.

The lower case letter used to identify the modules distinguishes multiple appearances of the same type of module in the same process.

FIG. 1 is a block flow diagram of a process in accordance with the present invention for converting 1230za to E-1233zd using a liquid phase fluorination step. The Figure incorporates the process modules described above. FIG. 1 discloses a process wherein 1230za and HF are fed to reaction module RFL-1. Typically, the reaction takes place in a predominantly HF rich medium without a catalyst. The HCl and the 1233zd/HF exit the top of the rectification column of RFL-1. The vapor effluent of RFL-1 enters DH-1 to remove HCl as a pure overhead product. The bottoms of DH-1 consists primarily of 1233zd (both E and Z isomers) and HF at a near azeotropic composition. This is fed to module PS-1 to effect a liquid phase separation. The top HF rich phase is sent to module DA-1a, where HF is separated as a bottoms stream for recycle to the reactor. The overhead azeotrope of 1233zd and HF is recycled back to DH-1 to allow any residual HCl and light organics to be stripped out in this column before the azeotrope gets recycled to phase separation. The bottoms stream from PS-1 goes to module DA-1b, which removes an organic stream devoid of HF as a bottoms stream. The overhead from DA-1b is recycled to DH-1 for the same reason that the DA-1a azeotrope was recycled to DH-1. The bottoms of DA-1b is sent to process module DS-1 that separates any heavies from the 1233zd. The overhead from DS-1 is E-1233zd, the desired trans isomer. The Z-1233zd is higher boiling and is recovered for feeding to process module RI-1. The effluent from the isomerization reactor is recycled to DS-1, which effects the separation of the E and Z isomers.

Figure 2:
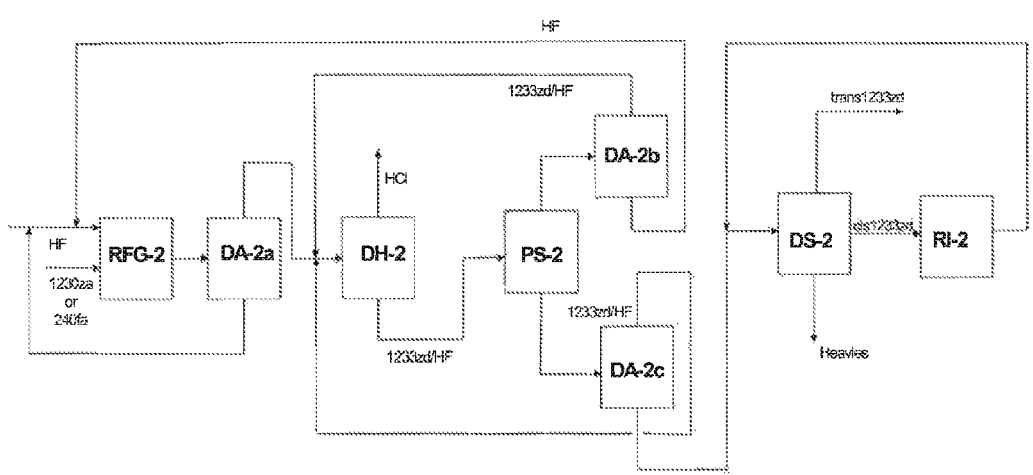
FIG. 2 is schematic of a gas phase process in accordance with the present invention.

FIG. 2 is a block flow diagram of a process in accordance with the present invention for converting 1230za or 240fa to E-1233zd using a gas phase fluorination step. The Figure incorporates the process modules described above. In FIG. 2 the process is similar to FIG. 1 except, for example, the liquid phase fluorination reactor (RFL-1) is replaced by a gas phase fluorination reactor (RFG-1) and azeotropic distillation column (DA-2a). The process as outlined by FIG. 2 comprises feeding 1230za and/or 240fa and HF to reaction module RFG-2. The reaction takes place in a gas phase with a catalyst. The reactor effluent consists of predominantly HCl, 1233zd, unreacted 1230za and excess HF. The reactor effluent of RFG-2 enters DA-2a to remove HF and unreacted F1230za as bottoms that is recycled to the reactor. The overhead, which consists predominantly of HCl and the azeotrope of HF and 1233zd (both E and Z isomers), is sent to DH-2, which removes HCl as a pure overhead product. The bottoms of DH-2 consists of primarily 1233zd (both E and Z isomers) and HF at a near azeotropic composition. This is fed to module PS-2 to effect a liquid phase separation. The top HF rich phase is sent to module DA-2b, where HF is separated as a bottoms stream for recycle to the reactor. The overhead azeotrope of 1233zd and HF is recycled back to DH-2 to allow any residual HCl and light organics to be stripped out in this column before the azeotrope gets recycled to phase separation. The bottoms stream from PS-2 goes to module DA-2c, which removes an organic stream devoid of HF as a bottoms stream. The overhead from DA-2c is recycled to DH-2 for the same reason that the DA-2b azeotrope was recycled to DH-2. The bottoms of DA-2c is sent to process module DS-2 that separates any heavies from the 1233zd. The overhead from DS-2 is E-1233zd—the desired trans isomer. The Z-1233zd is higher boiling and is recovered for feeding to process module RI-2. The effluent from the isomerization reactor is recycled to DS-2, which effects the separation of the E and Z isomers.

What we claim:

1. A process for manufacturing trans 1-chloro 3,3,3 trifluoro propene (E-1233zd) from 1,1,3,3-tetrachloropropene (1230za) and/or 1,1,1,3,3-pentachloropropane (240fa) comprising the steps of:
    forming a chloroalkane via addition of an olefin to a starting chloroalkane and reacting the chloroalkane to form 1,1,3,3-tetrachlororopropene (1230za, $CCl_2$=CH—$CHCl_2$) and/or 1,1,1,3,3-pentachoropropane (240fa); followed by
    fluorination of 1,1,3,3-tetrachloropropene (1230za) and/or 1,1,1,3,3-pentachloropropane (240fa) to a mixture comprising cis 1233zd (Z-1233zd) and trans 1233zd (E-1233zd); followed by
    separation of said cis 1233zd (Z-1233zd) from said trans 1233zd (E-1233zd); followed by
    isomerization of said cis 1233zd (Z-1233zd) to form trans 1233zd (E-1233zd).

2. The process of claim 1 wherein said starting chloroalkane is selected form the group consisting of carbon tetrachloride, chloroform and methyl chloride.

3. The process of claim 1 wherein said olefin is selected form the group consisting of ethylene, vinyl chloride, 1,1-dichloroethene, 1,2-dichloroethene, trichloroethylene, tetrachlorethylene and chlorofluoroethylene.

4. The process of claim 1 wherein said addition is in the presence of at least one catalyst.

5. The process of claim 4 wherein said at least one catalyst is selected from the group consisting of cuprous compounds, iron powder, iron chloride, organonickel compounds and organocopper compounds.

6. The process of claim 1 wherein said reacting comprises chlorination or dehydrochlorination.

7. The process of claim 1 wherein said starting chloroalkane is selected from the group consisting of 1,1,1,3-tetrachloropropane (250fb), 1,1,1,3,3-pentachloropropane (240fa), 1,1,1,2,3-pentachloropropane (240 db) and 1,1,1,2,3,3-hexachloropropane (230da).

8. The process of claim 1 wherein said isomerization process is carried out in the gas phase or the liquid phase.

9. The process of claim 8 wherein said isomerization is carried out in a liquid phase with a homogeneous catalysts selected from the group consisting of soluble Lewis acid catalysts and Bronsted acid catalysts.

10. The process of claim 9 wherein said soluble Lewis acid catalyst is selected from $Sb^V$; $Ti^{IV}$; $Sn^{IV}$; $Mo^{VI}$; $Nb^V$; $Ta^V$; oxide supported catalysts; fluorinated alumina; fluorinated chromia; prefluorinated activated carbon; graphite carbon; SiC; $Sb^5$.

11. The process of claim 10 wherein said oxide supported catalyst is selected from the group consisting of $Al_2O_3$ and $TiO_2$.

12. The process of claim 9 wherein said Bronsted acid catalyst is selected from the group consisting of triflic acid, methane sulfonic acid, sulfuric acid and sulfonic acid.

13. The process of claim 8 wherein said isomerization is carried out in the liquid phase in the absence of a catalyst.

14. The process of claim 8 wherein said isomerization is carried out in the gas phase with a high surface area heterogeneous Cr catalyst, supported or unsupported.

15. The process of claim 9 wherein said catalyst further comprising a co-catalyst selected from the group consisting of Co, Ni, Zn and Mn.

* * * * *